United States Patent
Hori

(10) Patent No.: US 11,484,687 B2
(45) Date of Patent: Nov. 1, 2022

(54) CATHETER

(71) Applicant: ASAHI INTECC CO., LTD., Seto (JP)

(72) Inventor: Takayuki Hori, Seto (JP)

(73) Assignee: ASAHI INTECC CO., LTD., Seto (JP)

(*) Notice: Subject to any disclaimer, the term of this patent is extended or adjusted under 35 U.S.C. 154(b) by 0 days.

(21) Appl. No.: 16/937,199

(22) Filed: Jul. 23, 2020

(65) Prior Publication Data

US 2020/0353210 A1  Nov. 12, 2020

Related U.S. Application Data

(63) Continuation of application No. PCT/JP2018/002565, filed on Jan. 26, 2018.

(51) Int. Cl.
*A61M 25/00* (2006.01)
*A61M 25/09* (2006.01)

(52) U.S. Cl.
CPC .... *A61M 25/0053* (2013.01); *A61M 25/0023* (2013.01); *A61M 25/09* (2013.01); *A61M 2025/09083* (2013.01)

(58) Field of Classification Search
CPC .............. A61M 25/0053; A61M 25/09; A61M 2025/09083; A61M 25/0138; A61M 25/0012; A61M 25/0074; A61M 25/005; A61M 25/0054; A61M 25/0023; A61M 25/0045; A61M 25/008
See application file for complete search history.

(56) References Cited

U.S. PATENT DOCUMENTS

| | | | | |
|---|---|---|---|---|
| 2002/0072689 A1* | 6/2002 | Klint | ............... | A61M 25/09025 600/585 |
| 2007/0049847 A1* | 3/2007 | Osborne | ............... | A61M 25/09 600/585 |
| 2008/0004546 A1 | 1/2008 | Kato | | |
| 2014/0276117 A1* | 9/2014 | Burkett | ............... | A61B 5/6852 600/479 |
| 2015/0273182 A1* | 10/2015 | Watanabe | ........... | A61M 25/005 604/527 |
| 2015/0306347 A1 | 10/2015 | Yagi | | |
| 2015/0352326 A1* | 12/2015 | Tegg | ................. | A61M 25/0147 604/95.04 |

(Continued)

FOREIGN PATENT DOCUMENTS

| CN | 101099877 A | 1/2008 |
|---|---|---|
| CN | 105013061 A | 11/2015 |

(Continued)

*Primary Examiner* — Nathan R Price
*Assistant Examiner* — Justin L Zamory
(74) *Attorney, Agent, or Firm* — Oliff PLC

(57) ABSTRACT

A catheter includes a hollow shaft, a multi-thread coil body covering the hollow shaft, and a cover member covering the multi-thread coil body. The multi-thread coil body includes a ring-shaped or substantially hollow cylindrical joint part in which distal ends of a plurality of element wires are joined in a circumferential direction, a coil main body located at a proximal side of the joint part in an axial direction, in which an outer shape of a cross section of each of the plurality of element wires is circular, and a transition part located between the joint part and the coil main body, in which a width of at least one of the plurality of element wires widens toward a distal end of the element wire.

12 Claims, 5 Drawing Sheets

(56) References Cited

U.S. PATENT DOCUMENTS

2016/0279383 A1* 9/2016 Kanazawa .......... A61M 25/001
2017/0353017 A1* 12/2017 Ward ....................... D07B 1/18

FOREIGN PATENT DOCUMENTS

| CN | 105983168 A | 10/2016 |
| JP | 2003-520651 A | 7/2003 |
| JP | 2012-147956 A | 8/2012 |
| JP | 2016-179170 A | 10/2016 |
| KR | 10-2008-0066873 A | 7/2008 |
| WO | 01/54761 A2 | 8/2001 |
| WO | 2007/056302 A2 | 5/2007 |

* cited by examiner

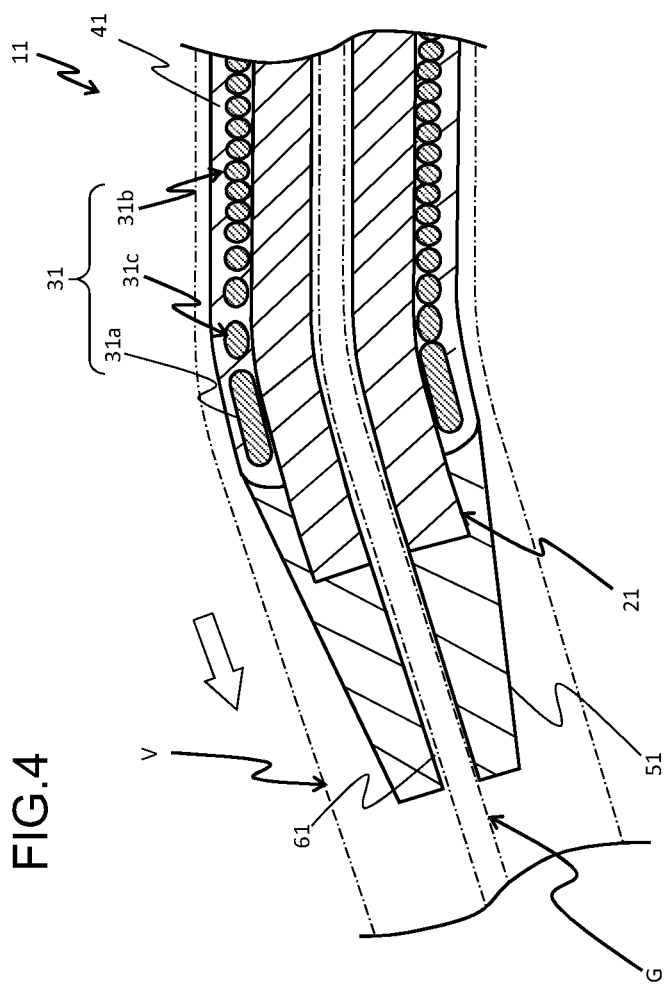

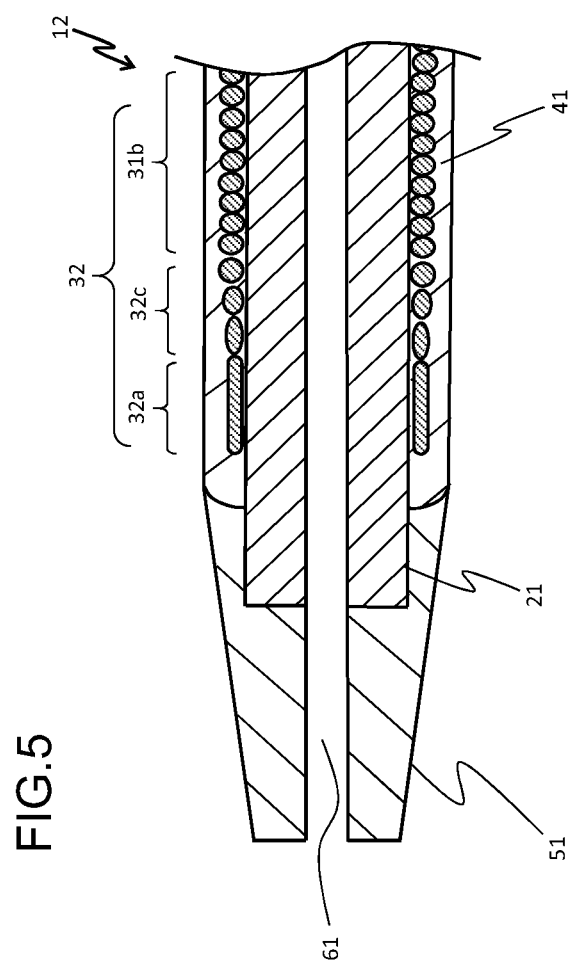

CATHETER

CROSS REFERENCE TO RELATED APPLICATION

This application is a continuation application of International Application No. PCT/JP2018/002565, filed Jan. 26, 2018. The contents of the application are incorporated herein by reference in its entirety.

BACKGROUND

The disclosed embodiments relate to a catheter.

For example, when treating an abnormality in a blood vessel such as chronic total occlusion (CTO), after first passing a guide wire through the blood vessel to be treated, a catheter is passed along the guide wire to a destination to perform the desired treatment.

As an example of such a catheter, Japanese Patent Document JP2012-147956 discloses a catheter in which a winding layer formed by winding wire materials into a coil shape is arranged on an outer peripheral surface of an inner layer that defines a main lumen through which a guide wire or the like is passed, and ring-shaped joining members are joined at fixed intervals on an outer periphery of the winding layer.

The above-described technique is excellent in that it is possible to prevent unwinding of the wire materials, because a joint part where the wire materials and the joint members are joined is provided and adjacent wire materials are fixed at intervals.

SUMMARY

However, in the conventional catheter as described above, although it is possible to prevent unwinding of the wire materials, the stiffness of the winding layer changes sharply at a boundary between the joint part and a part of the wire material other than the joint part. This causes the bending stress to be concentrated on the boundary due to an external force when the catheter advances into a curved body cavity, which may result in damage.

The disclosed embodiments have been made in view of the above circumstances, and an object thereof is to provide a catheter capable of preventing breakage of a multi-thread coil body while preventing unwinding of an element wire.

To achieve the above object, a catheter according to the disclosed embodiments includes: a hollow shaft; a multi-thread coil body wound around the hollow shaft to cover an outer periphery of the hollow shaft; and a cover member covering the multi-thread coil body, the cover member provided around the outer periphery of the hollow shaft. The multi-thread coil body includes: a ring-shaped or substantially hollow cylindrical joint part in which distal ends of a plurality of element wires forming the multi-thread coil body are joined in a circumferential direction; a coil main body located at a proximal side of the joint part in an axial direction, in which an outer shape of a cross section of each of the plurality of element wires is circular; and a transition part located between the joint part and the coil main body, in which a width of at least one of the plurality of element wires widens toward a distal end direction.

In the present specification, the "distal end direction" means an axial direction of the catheter in which the joint part is located with respect to the coil main body of the multi-thread coil body. Further, the "proximal end direction" means an axial direction of the catheter opposite to the distal end direction. The "width" means a length of a cross section of a winding wire in a direction perpendicular to a radial direction of the hollow shaft. The "thickness" means a length of the cross section of the winding wire in a radial direction of the hollow shaft. It is noted that the above-described winding wire may be a single solid element wire or a twisted wire formed from a plurality of wires.

BRIEF DESCRIPTION OF THE DRAWINGS

FIG. 4 is a schematic cross-sectional view illustrating an example of the usage state of the catheter in FIG. 1.

FIG. 5 is an enlarged schematic cross-sectional view illustrating a part of a catheter of the disclosed embodiments.

DETAILED DESCRIPTION OF EMBODIMENTS

Figure 1:
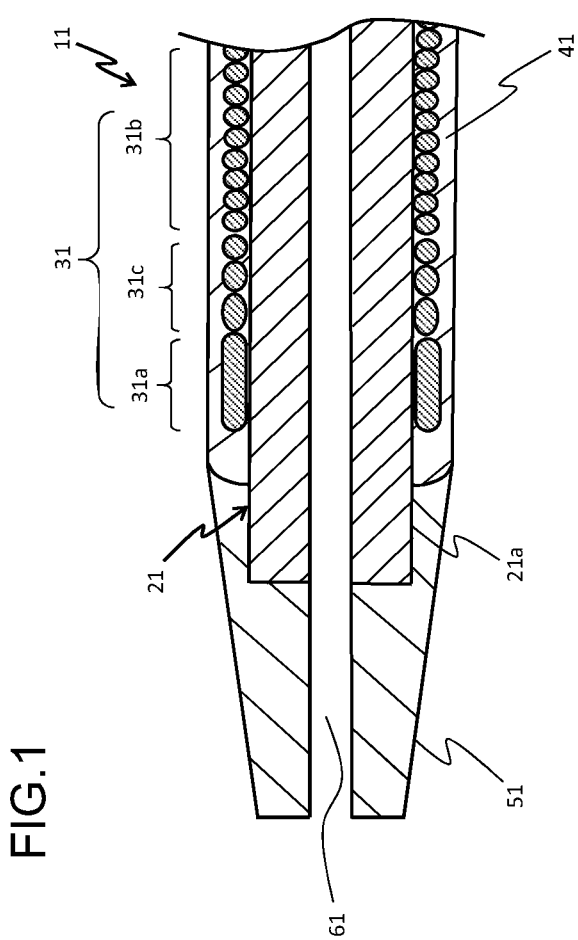
FIG. 1 is an enlarged schematic cross-sectional view illustrating a part of a catheter of the disclosed embodiments.

A catheter according to the present disclosure includes: a hollow shaft; a multi-thread coil body wound around the hollow shaft to cover an outer periphery of the hollow shaft; and a cover member covering the multi-thread coil body, the cover member provided around the outer periphery of the hollow shaft. The multi-thread coil body includes a ring-shaped or substantially hollow cylindrical joint part in which distal ends of a plurality of element wires forming the multi-thread coil body are joined in a circumferential direction; a coil main body located at a proximal side of the joint part in axial direction, in which an outer shape of a cross section of each of the plurality of element wires is circular; and a transition part located between the joint part and the coil main body, in which a width of at least one of the plurality of element wires widens toward a distal end of the element wire.

Hereinafter, embodiments of the present invention will be described with reference to the drawings, but the present invention shall not be limited only to the embodiments described in the drawings.

FIG. 1 is an enlarged schematic cross-sectional view illustrating a part of a catheter of the disclosed embodiments. As illustrated in FIG. 1, a catheter 11 generally includes a hollow shaft 21, a multi-thread coil body 31, a cover member 41, and a distal tip 51.

A guide wire inserted in advance into a body cavity such as a blood vessel is inserted into the hollow shaft 21. Specifically, as illustrated in FIG. 1, the hollow shaft 21 is, for example, a tubular member having a lumen 61 for inserting a guide wire inside, and the lumen 61 extends along the axial direction in a substantially central portion of a cross section taken perpendicular to the longitudinal axis of the hollow shaft 21. A connector (not illustrated) is connected to an end of the hollow shaft 21 in a proximal end direction, and various procedures are performed through the connector.

As for dimensions of parts of the hollow shaft 21, the total length may be 1350 to 1550 mm, the outer diameter may be 0.45 to 0.65 mm, and the inner diameter (the diameter of the lumen 61) may be 0.36 to 0.46 mm. For example, the hollow shaft 21 may have a total length of 1550 mm, an outer diameter of 0.62 mm, and an inner diameter (the diameter of the lumen 61) of 0.40 mm.

Since the hollow shaft 21 is inserted into a body cavity such as a blood vessel, it is preferable that the material of the hollow shaft 21 has antithrombogenicity, flexibility, and biocompatibility. For example, it is possible to employ, as a material of the hollow shaft 21, a resin material such as a polyamide resin, polyolefin resin, polyester resin, polyurethane resin, silicone resin, fluororesin, or the like; or a metal material such as hypotube or the like. Among these, from the viewpoint of improving the slidability of the guide wire or the like inserted into the lumen 61, a fluororesin is preferable, and polytetrafluoroethylene (PTFE) is more preferable.

Figure 2:
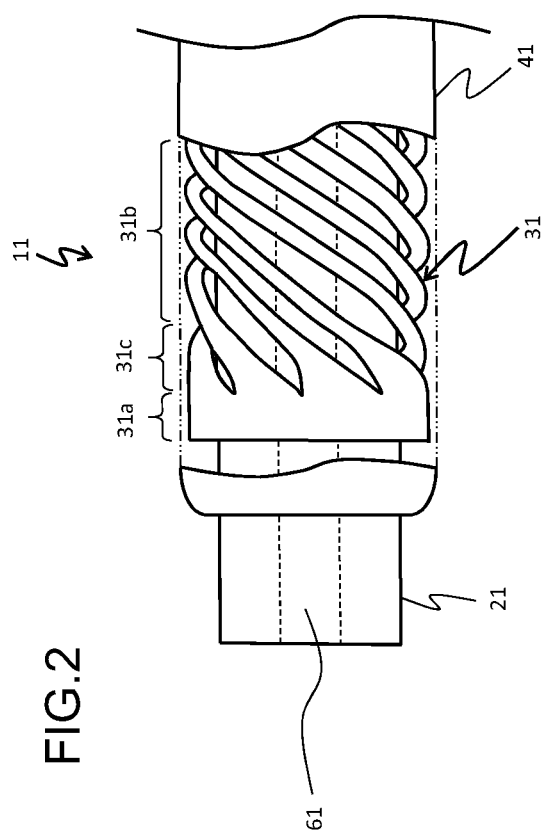
FIG. 2 is an enlarged schematic side view illustrating a hollow shaft and a multi-thread coil body of the catheter in FIG. 1.

The multi-thread coil body 31 provides an effect of reinforcing the hollow shaft 21 and enhancing the torquability. As illustrated in FIG. 2, the multi-thread coil body 31 is wound around the hollow shaft 21 to cover an outer periphery 21a of the hollow shaft 21, and includes a joint part 31a, a coil main body 31b, and a transition part 31c.

Figure 3A:
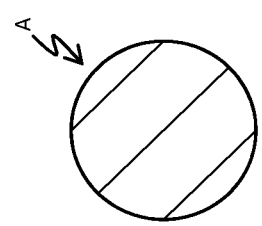
FIG. 3A is a schematic view illustrating a cross-sectional shape of a winding wire A in a coil main body.
Figure 3B:
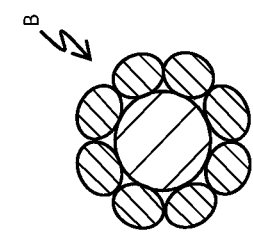
FIG. 3B is a schematic view illustrating a cross-sectional shape of a winding wire B in the coil main body.
Figure 3C:
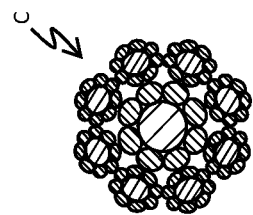
FIG. 3C is a schematic view illustrating a cross-sectional shape of a winding wire C in the coil main body.

Examples of the multi-thread coil body 31 to be employed include a coil body in which a plurality of solid wires (element wires) (hereinafter, also referred to as "winding wire A") (see FIG. 3A) are spirally wound; a coil body in which a twisted wire (hereinafter, also referred to as "winding wire B") (see FIG. 3B) twisted using a plurality of solid wires is spirally wound; and a coil body in which a plurality of twisted wires (hereinafter, also referred to as "winding wire C") (see FIG. 3C) are spirally wound, the twisted wire being formed by twisting a plurality of solid wires. Among them, as the multi-thread coil body 31, the winding wire A having the largest metal occupying area in the cross section is preferable from a viewpoint of improving the torquability, the winding wire C is preferable from a viewpoint of improving the flexibility, and the winding wire B is preferable from a viewpoint of striking a good balance between the torquability and the flexibility.

As for the diameter of the element wires forming the multi-thread coil body 31, for example, it is possible to employ the winding wire A having a diameter of 0.030 to 0.120 mm, the winding wire B having a diameter of 0.010 to 0.060 mm, and the winding wire C having a diameter of 0.005 to 0.030 mm.

The material of the element wires forming the multi-thread coil body 31 is not particularly limited as long as the material has antithrombogenicity and biocompatibility along with flexibility. Examples of the material include stainless steel such as SUS304 and SUS316; a superelastic alloy such as an Ni—Ti alloy; gold, platinum, tungsten, and alloys thereof; a metal such as a nickel-cobalt alloy, and the like.

The joint part 31a is a ring-shaped or substantially hollow cylindrical part in which the distal ends of the plurality of element wires forming the multi-thread coil body 31 are joined in a circumferential direction. A method of forming the joint part 31a is not particularly limited, and examples of the method include a method in which an end of an element wire in the distal end direction of the coil body 31 is irradiated with laser light to be heated and melted, and the end is then connected in the circumferential direction to form a ring shape or a substantially hollow cylindrical shape, and a method in which a metal brazing material such as an Sn—Pb alloy, a Pb—Ag alloy, an Sn—Ag alloy, or an Au—Sn alloy is used to connect the above-described end of the element wire in the circumferential direction by brazing to form a ring shape or a substantially hollow cylindrical shape.

The coil main body 31b is located at a position in the proximal end direction of the joint part 31a and is a part in which the outer shape of a cross section of each of the element wires is circular. The coil main body 31b is formed by spirally winding the element wires having a constant outer diameter.

The transition part 31c is located between the joint part 31a and the coil main body 31b, and is a part in which a width of at least one of the plurality of element wires widens toward the distal end of the element wire. Specifically, as illustrated in FIG. 2, the transition part 31c has a distal end continuous with the joint part 31a and a proximal end continuous with the coil main body 31b, and the width of the winding wires forming the multi-thread coil body 31 gradually increases toward the distal end direction in the transition part 31c.

Each winding wire shown in FIG. 2 is schematically illustrated with one line (one solid wire). However each of the winding wires described above as winding wire A to C is actually configured with one or more element wires. The width of the winding wire widens toward the distal end direction. More specifically, the width of at least one element wire in the winding wire widens toward the distal end direction.

Here, the width of some element wires among the plurality of element wires forming the multi-thread coil body 31 may increase gradually toward the distal end direction, or the width of each of all of the plurality of element wires may increase gradually toward the distal end direction. As a result, a difference in stiffness between the joint part 31a and the coil main body 31b can be gradually alleviated by using all the element wires in the transition part 31c. And thus it is possible to prevent the multi-thread coil body 31 from being broken due to a steep stiffness gradient.

The present embodiment illustrates the catheter 11 including the multi-thread coil body 31 in which ten element wires (winding wires A) that are made of SUS304 and have a diameter of 0.090 mm are spirally wound together, and the distal ends of the element wires are joined in the circumferential direction to have a substantially hollow cylindrical shape.

The cover member 41 is provided around the outer periphery 21a of the hollow shaft 21, covers the multi-thread coil body 31, and fixes the multi-thread coil body 31 to the outer periphery 21a of the hollow shaft 21.

The material of the cover member 41 preferably has antithrombogenicity, flexibility and biocompatibility. For example, a resin such as a polyamide, polyamide elastomer, polyester, polyester elastomer, polyurethane, and polyurethane elastomer, or the like can be employed.

An example of a method of forming the cover member 41 includes a method in which an extruder is used to cover, with a thermoplastic resin such as a polyamide, the coil body 31 arranged on the outer periphery 21a of the hollow shaft 21.

The distal tip 51 is provided to cover at least a part of the outer periphery of the distal end of the hollow shaft 21. Specifically, the distal tip 51 may be formed in a spire shape, a substantially truncated cone shape (see FIG. 1), or the like in which the diameter decreases toward the distal end direction to enable the catheter 11 to smoothly advance into a body cavity such as a blood vessel and easily pass through a hard region such as a calcified lesion.

Examples of the material forming the distal tip 51 include a resin material such as polyurethane and polyurethane elastomer; stainless steel such as SUS304 and SUS316; gold, platinum, tungsten, and alloys thereof; a nickel-chromium alloy, and the like.

It is possible to use the catheter 11 in the same manner as well-known catheters. For example, as illustrated in FIG. 4, after one end (the distal end) of a guide wire G is inserted into a blood vessel V in advance and then advanced up to a site to be treated, the other end (the proximal end) of the guide wire G exposed to the outside of the body is inserted into an opening of the lumen 61 at the distal tip 51 of the catheter 11. Next, the catheter 11 is inserted into the blood vessel V, and is pushed along the guide wire G up to the site to be treated in the blood vessel V to provide a predetermined treatment.

With the above-described configuration of the catheter 11, it is possible to gradually alleviate a difference in stiffness between the joint part 31a and the coil main body 31b while preventing unwinding of the element wires. And thus the breakage of the multi-thread coil body 31 (particularly, the breakage at the proximal end of the joint part) that is likely to occur due to a steep stiffness gradient can be prevented.

FIG. 5 is an enlarged schematic cross-sectional view illustrating a part of a catheter of the disclosed embodiments. As illustrated in FIG. 5, a catheter 12 generally includes the hollow shaft 21, a multi-thread coil body 32, the cover member 41, and the distal tip 51. The shape of the multi-thread coil body 32 of the catheter 12 is different from that of the catheter 11. The configuration other than the shape of the multi-thread coil body 32 is the same as that of the catheter 11. Therefore, the same parts are designated by the same reference numerals and detailed description thereof will not be repeated.

As illustrated in FIG. 5, the multi-thread coil body 32 is wound around the hollow shaft 21 to cover the outer periphery of the hollow shaft 21, and has a joint part 32a, the coil main body 31b, and a transition part 32c.

The joint part 32a is a ring-shaped or substantially hollow cylindrical part in which distal ends of a plurality of element wires forming the multi-thread coil body 32 are joined in the circumferential direction. The joint part 32a is formed so that a thickness of the joint part 32a is smaller than a diameter of any of the plurality of wire elements in the coil main body 31b.

Similarly to the catheter 11, the transition part 32c is located between the joint part 32a and the coil main body 31b, where a width of at least one of the plurality of element wires widens toward the distal end direction. Here, it is preferable that a thickness of at least one of the plurality of element wires in the transition part 32c decreases gradually toward the distal end direction until the thickness is the same as the thickness of the joint part 32a, and it is more preferable that a thickness of each of all of the plurality of element wires decreases gradually toward the distal end direction until the thickness is the same as the thickness of the joint part 32a.

As illustrated in FIG. 5, the joint part 32a according to the present embodiment is a substantially hollow cylindrical joint part 32a having a thickness smaller than a diameter of any of the element wires in the coil main body 31b, and the thickness of each of all of the element wires in the transition part 32c changes linearly from the thickness of the element wires at a boundary between the transition part 32c and the coil main body 31b to a thickness of the joint part 32a at a boundary between the transition part 32c and the joint part 32a.

In this way, the thickness of the element wires in the transition part 32c decreases gradually toward the distal end direction until the thickness is the same as the thickness of the joint part 32a, and thus, it is possible to further reduce the stiffness gradient.

With the above-described configuration of the catheter 12, it is possible to reduce a difference in stiffness between the joint part 32a and the coil main body 31b owing to a small thickness of the joint part 32a while preventing unwinding of the element wires. This can more reliably prevent the breakage of the multi-thread coil body 32 (particularly, the breakage at the proximal end of the joint part) as a result of the reduction in the stiffness gradient.

The present disclosure is not limited to the configuration of the above-described embodiments, but is indicated by the claims, and is intended to include all modifications within meanings and the scope equivalent to the claims.

For example, in the above-described embodiments, the catheters 11 and 12 provided with the distal tip 51 have been described. However, as long as a catheter can smoothly advance into a body cavity, a catheter without a distal tip may also be employed.

Further, in the above-described embodiments, the catheters 11 and 12 in which the multi-thread coil bodies 31 and 32 and the hollow shaft 21 are fixed by the cover member 41 have been described. However, for example, a catheter in which a multi-thread coil body and a hollow shaft are fixed by another method, such as a catheter in which a multi-thread coil body and a hollow shaft are brazed by using a brazing material may be employed.

In addition, in the above-described embodiments, the catheters 11 and 12 provided with the multi-thread coil bodies 31 and 32 have been described. However, a catheter provided with a single-thread coil body in which a single solid wire (element wire) is spirally wound can also be expected to provide a similar effect to that of the catheter provided with the multi-thread coil body described above.

The invention claimed is:

1. A catheter comprising:
a hollow shaft; and
a coil body that is a multi-thread coil body disposed around an outer periphery of the hollow shaft and comprising a plurality of spirally wound element wires, the coil body comprising:
a joint part having a ring shape or a substantially hollow cylindrical shape, at which distal ends of the plurality of element wires are fused together in a circumferential direction;
a coil main body located at a proximal side of the joint part in an axial direction of the coil body, in which an outer shape of a cross section of each of the plurality of element wires taken in the axial direction is circular; and
a transition part located between the joint part and the coil main body, in which a width of at least one of the plurality of element wires widens toward a distal end of the coil body,
wherein a thickness of the joint part is smaller than a diameter of any of the plurality of element wires in the coil main body.

2. The catheter according to claim 1, wherein a width of each of all of the plurality of element wires in the transition part widens toward the distal end of the element wire.

3. The catheter according to claim 1, wherein a thickness of at least one of the plurality of element wires in the transition part decreases toward the distal end of the element wire until the thickness is the same as the thickness of the joint part.

4. The catheter according to claim 3, wherein a thickness of each of all of the plurality of element wires in the transition part decreases toward the distal end of the element wire until the thickness is the same as the thickness of the joint part.

5. The catheter according to claim 1, further comprising a cover member covering at least a part of the coil body and provided on the outer periphery of the hollow shaft.

6. The catheter according to claim 1, wherein the thickness of the joint part is configured to reduce a difference in stiffness between the joint part and the coil main body.

7. A catheter comprising:
a hollow shaft; and
a coil body that is a multi-thread coil body disposed around an outer periphery of the hollow shaft and comprising a plurality of spirally wound element wires, the coil body comprising:
a joint part having a ring shape or a substantially hollow cylindrical shape, at which distal ends of the plurality of element wires are joined in a circumferential direction;
a coil main body located at a proximal side of the joint part in an axial direction of the coil body, in which an outer shape of a cross section of each of the plurality of element wires taken in the axial direction is circular; and
a transition part located between the joint part and the coil main body, in which a width of at least one of the plurality of element wires widens toward a distal end of the coil body,
wherein a thickness of the joint part is smaller than a diameter of any of the plurality of element wires in the coil main body and is configured to reduce a difference in stiffness between the joint part and the coil main body.

8. The catheter according to claim 7, wherein a width of each of all of the plurality of element wires in the transition part widens toward the distal end of the element wire.

9. The catheter according to claim 7, wherein a thickness of at least one of the plurality of element wires in the transition part decreases toward the distal end of the element wire until the thickness is the same as the thickness of the joint part.

10. The catheter according to claim 9, wherein a thickness of each of all of the plurality of element wires in the transition part decreases toward the distal end of the element wire until the thickness is the same as the thickness of the joint part.

11. The catheter according to claim 7, further comprising a cover member covering at least a part of the coil body and provided on the outer periphery of the hollow shaft.

12. The catheter according to claim 7, wherein the distal ends of the plurality of element wires are connected in the circumferential direction to form the joint part.

* * * * *